United States Patent [19]

Raymond

[11] 4,215,231

[45] Jul. 29, 1980

[54] CO-PRODUCTION OF ETHYLENE AND BENZENE

[75] Inventor: Robert F. Raymond, Arlington Hts., Ill.

[73] Assignee: UOP Inc., Des Plaines, Ill.

[21] Appl. No.: 43,210

[22] Filed: May 29, 1979

Related U.S. Application Data

[63] Continuation-in-part of Ser. No. 894,264, Apr. 7, 1978, Pat. No. 4,167,533.

[51] Int. Cl.$^2$ .............................................. C07C 3/30
[52] U.S. Cl. ................................... 585/251; 585/258; 585/319; 585/324; 585/488; 585/650; 208/67
[58] Field of Search ............... 585/251, 258, 319, 324, 585/488, 650; 208/67

[56] References Cited

U.S. PATENT DOCUMENTS

| 3,310,592 | 3/1967 | Fukuda et al. | 585/251 |
| 3,472,909 | 10/1969 | Raymond | 585/251 |
| 3,492,220 | 1/1970 | Lempert | 208/144 |
| 3,496,095 | 2/1970 | Lewis | 208/57 |
| 3,513,217 | 5/1970 | Raymond | 585/251 |
| 3,625,879 | 12/1971 | Horne et al. | 585/251 |

Primary Examiner—C. Davis
Attorney, Agent, or Firm—James R. Hoatson, Jr.; Robert W. Welch; William H. Page, II

[57] ABSTRACT

Ethylene and maximum benzene are co-produced via a combination process involving (1) thermal cracking, or pyrolysis, (2) aromatic hydrocarbon separation, or extraction, and, (3) dealkylation of alkyl-substituted aromatics to yield additional benzene. Unconverted feed paraffins are recycled to thermal cracking for additional ethylene and benzene production.

14 Claims, 1 Drawing Figure

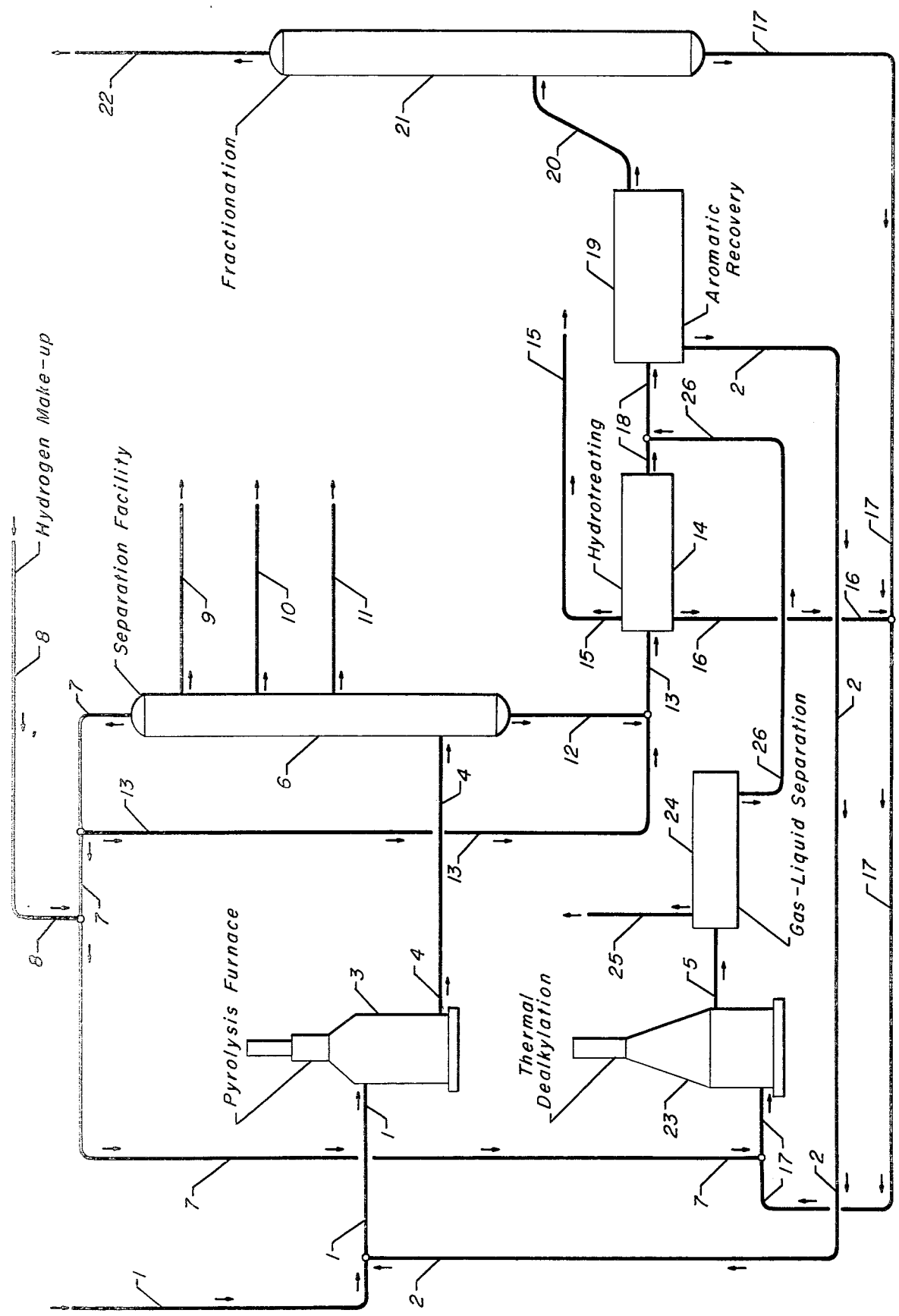

CO-PRODUCTION OF ETHYLENE AND BENZENE

CROSS-REFERENCE TO RELATED APPLICATION

This is a Continuation-In-Part of a copending application Ser. No. 894,264 filed Apr. 7, 1978, now U.S. Pat. No. 4,167,533.

APPLICABILITY OF INVENTION

Ethylene and benzene are extensively employed in the petroleum and petrochemical industries as building blocks for a multitude of organic compounds. Ethylene is perhaps the fifth highest-volume chemical produced in the United States, while benzene ranks about thirteenth. Although ethylene may be produced via the thermal cracking or normally gaseous paraffins, pyrolysis feedstocks predominate in normally liquid hydrocarbons boiling up to a temperature of about 525° F. (274° C.). The principal source of benzene, in addition to other mono-nuclear aromatics, resides in the catalytic reforming of hydrotreated naphtha fractions, or distillates, boiling up to about 400° F. (204° C.). However, benzene and the other aromatics appear as a co-product in the pyrolysis of normally liquid hydrocarbons for ethylene production. Kerosene boiling range hydrocarbons, 400° F. (204° C.) to 525° F. (274° C.), may serve as feed components to the present combination process. Naphtha boiling range charge stocks, pentanes and heavier material up to about 400° F. (204° C.), are generally preferred. Applicable charge stocks include: straight-run, full boiling range naphthas; light naphthas having an end boiling point in the range of about 200° F. (93° C.) to about 300° F. (149° C.); and, heavy naphthas having an initial boiling point above about 200° F. (93° C.) and an end boiling point above about 300° F. (149° C.). It is understood that the viability of the present combination process does not rely upon the precise character of the hydrocarbonaceous charge stock.

OBJECTS AND EMBODIMENTS

A principal object of the process encompassed by my inventive concept resides in the maximum production of benzene from the normally liquid pyrolysis co-product. A corollary objective is to maximize ethylene production by recycling a paraffinic concentrate following separation of aromatic hydrocarbons therefrom.

Another object of the present invention is to provide a combination process which approaches, and often attains self-sufficiency with respect to hydrogen requirements.

In one of its broad aspects, the present invention embodies a process for the co-production of ethylene and benzene from a hydrocarbonaceous feedstock which comprises charging said feedstock to a thermal cracking zone at conditions selected to convert paraffinic hydrocarbons into lower boiling, normally vaporous hydrocarbons; introducing the thermal cracking zone effluent into a first separation zone and separating a hydrogen-rich vaporous phase, ethylene, and a normally liquid phase containing aromatic hydrocarbons; recovering the separated ethylene; introducing said normally liquid phase into a second separation zone, concentrating the aromatic hydrocarbons therein, and separating unconverted non-aromatic hydrocarbons; introducing said aromatic hydrocarbons into a third separation zone and separating benzene and alkylaromatic hydrocarbons therein; recovering the separated benzene; reacting said alkylaromatic hydrocarbons in admixture with at least a portion of said hydrogen-rich vaporous phase in a dealkylation reaction zone at conditions selected to convert said alkylaromatic hydrocarbons into benzene; and introducing the dealkylation zone effluent into said second separation zone in combination with the aforesaid normally liquid phase introduced thereto.

In another embodiment, the dealkylation zone effluent is introduced into a gas-liquid separation zone wherein a vapor phase comprising normally gaseous hydrocarbons is separated and a normally liquid hydrocarbon phase is recovered and introduced into said second separation zone in combination with the aforesaid normally liquid phase introduced thereto.

A further embodiment relates to a process for the co-production of ethylene and benzene from a hydrocarbonaceous feedstock which comprises charging said feedstock to a thermal cracking zone at conditions selected to convert paraffinic hydrocarbons into lower boiling, normally vaporous hydrocarbons; introducing the thermal cracking zone effluent into a first separation zone and separating a hydrogen-rich vaporous phase, ethylene, and a normally liquid phase containing aromatic hydrocarbons; recovering the separated ethylene; treating said normally liquid phase in admixture with a portion of said hydrogen-rich vaporous phase in a hydrotreating zone at hydrotreating conditions selected to saturate olefins and convert sulfurous compounds to hydrogen sulfide and hydrocarbons, separating hydrogen sulfide and recovering the hydrotreated normally liquid phase; introducing said hydrotreated normally liquid phase into a second separation zone, concentrating the aromatic hydrocarbons therein, and separating unconverted non-aromatic hydrocarbons; introducing said aromatic hydrocarbons into a third separation zone and separating benzene and alkylaromatic hydrocarbons therein; recovering the separated benzene; reacting said alkylaromatic hydrocarbons in admixture with at least a portion of said hydrogen-rich vaporous phase in a dealkylation reaction zone at conditions selected to convert said alkylaromatic hydrocarbons into benzene; and introducing the dealkylation zone effluent into a gas-liquid separation zone wherein a vapor phase comprising normally gaseous hydrocarbons is separated, and a normally liquid hydrocarbon phase is recovered and introduced into said second separation zone in combination with the aforesaid hydrotreated normally liquid phase introduced thereto.

Other objects and embodiments will become evident, to those possessing the requisite skill in the art, from the following detailed description of the present combination process. In one such other embodiment, the unconverted non-aromatic hydrocarbons are admixed with said charge stock and subjected therewith to thermal cracking.

CITATION OF RELEVANT PRIOR ART

Candor compels recognition of the fact that the appropriate prior art is replete with illustrations of thermal cracking, aromatic hydrocarbon separation and hydrodealkylation techniques, both as individual processes and in combination with each other. Additionally, hydrotreating of the pyrolysis gasoline co-product, for sulfurous compound removal and olefin saturation, is thoroughly documented. Any attempt to delineate exhaustively the entire spectrum of the applicable prior art would at best be an exercise in futility. Therefore, since the present invention is directed toward a combination process, only that prior art which treats the principal combination of (1) thermal cracking, (2) aromatic separation and, (3) hydrodealkylation of alkyl-substituted aromatics will be discussed. Further, in view of the use of hydrotreating in one embodiment, the same will be discussed herein.

U.S. Pat. No. 3,310,592 (Cl. 260–672), issued Mar. 21, 1967, concerns itself with the maximization of benzene from steam cracked naphthas boiling from 140° F. (60° C.) to about 392° F. (200° C.). Essentially, the process involves (1) hydrogenation to saturate di-olefinic hydrocarbons, (2) more severe hydrogenative conversion to saturate mono-olefins and to dealkylate alkyl-substituted aromatics, (3) hydrodesulfurization and, (4) benzene recovery from the desulfurized product effluent.

U.S. Pat. No. 3,472,909 (Cl. 260–683), issued Oct. 14, 1969, initially commingles fresh naphtha feed and recycled pyrolysis gasoline, to provide a mixture having a Diene Value less than 10. The mixture is hydrogenated to saturate olefinic hydrocarbons, and aromatics are extracted from the hydrogenated effluent. Non-aromatic raffinate is then subjected to pyrolysis for ethylene production, followed by recycle of normally liquid hydrocarbons to the hydrogenating reaction system.

U.S. Pat. No. 3,492,220 (Cl. 208–144), issued Jan. 27, 1970, discloses a single, or two-stage hydrotreating technique for upgrading pyrolysis gasoline co-product. The two-stage technique is utilized in those instances where aromatics extraction is to follow.

In U.S. Pat. No. 3,513,217 (Cl. 260–683), issued May 19, 1970, the objective is to convert as much of the naphtha feedstock to ethylene as is possible. Therefore, the two-stage hydrotreating system also functions to saturate aromatic hydrocarbons, the naphthenic counterparts of which are more susceptible to cracking in the pyrolysis furnace. Unconverted hexane-plus material is recycled to the hydrotreating system.

Recovery of benzene from a selected cut of pyrolysis naphtha is described in U.S. Pat. No. 3,625,879 (Cl. 208–57), issued Dec. 7, 1971. The combination process involves (1) hydrogenation to saturate olefins, (2) reforming to convert naphthenes to aromatics and, (3) dealkylation of alkylaromatics. After recovery of benzene, heavier material is recycled to the hydrogenation system.

Perhaps the most relevant prior art is that exemplified by the disclosure of U.S. Pat. No. 3,496,095 (Cl. 208–57), issued Feb. 17, 1970. Here, a raw, unstable, olefinic feed containing sulfurous compounds is subjected to multiple-stage hydrogenation. Additional steps of the process are dependent upon the ultimate end use of the final product. Where motor fuel is desired, distillation facilities suffice. Should the desired product be an aromatic concentrate (referred to as a BTX fraction), extraction and one or more distillation steps is a suitable route. If the yield of benzene is to be maximized, hydrodealkylation is employed to remove the alkyl side chains (Column 1, Line 67 to Column 2, Line 11). Recognized, when the end result calls for aromatic extraction, is the recovery of the paraffinic raffinate for recycle to the steam cracking unit (Column 5, Lines 47–49). Dealkylation is described at Column 5, Line 59 through Column 6, Line 4.

Significantly, none of the foregoing delineated references recognizes, or appears to be capable of hydrogen self-sufficiency. As hereinafter set forth in greater detail, the present overall process utilizes about 75.0% by weight of the hydrogen produced in the pyrolysis system, allowing for about 33.0% of the hydrogen produced to be utilized in satisfying solution losses and venting. Specifically, when processing a full boiling range naphtha, the typical hydrogen yield is 0.9% by weight of the pyrolysis system feed, while 0.73% is the total consumed, inclusive of solution losses and venting.

SUMMARY OF INVENTION

As readily ascertained from the foregoing, aromatics recovery operations based upon ethylene co-product naphtha feedstocks commonly involve one or two stages of hydrotreating (or hydrogenation), followed by aromatics extraction (for BTX product), or direct hydrodealkylation of the entire mixture to yield maximum benzene and lighter hydrocarbons. Relative to benzene, aromatics extraction recovers lesser amounts of toluene, xylene and heavier aromatics; therefore, the unit manufacturing costs of these aromatics are often unattractive, or at best marginal. Hydrodealkylation solves the problems associated with the disposition of toluene and other heavier aromatics, but requires a source of hydrogen for dealkylating the aromatics and for cracking the non-aromatics.

The present combination is founded upon the recognition that the hydrogen produced during the pyrolysis operation is more than sufficient to satisfy the hydrogen requirements of dealkylation where the latter charges only the $C_7$-plus portion of the pyrolysis effluent. Furthermore, in those situations where hydrogenation is effected subsequent to the pyrolysis system, sufficient hydrogen remains to satisfy the hydrotreating needs. Additionally, I have recognized that non-aromatics in pyrolysis co-product naphtha concentrate in the lower-boiling end of the naphtha, since pyrolysis reactions necessitate higher severity as carbon number decreases. An illustration of this is the following composition of a typical naphtha co-product resulting from the pyrolysis of a feedstock originally "rich" in aromatics and naphthenes:

TABLE I

| Typical Co-Product Naphtha Composition | |
|---|---|
| Component | Wt. % |
| $C_5$ Hydrocarbons | 30.6 |
| $C_6$ Hydrocarbons | 15.8 |
| Benzene | 24.4 |
| $C_7$ Hydrocarbons | 6.8 |
| Toluene | 14.0 |
| $C_8$ Hydrocarbons | 0.7 |
| $C_8$ Aromatics | 3.7 |
| Heavier Hydrocarbons* | 4.0 |

*Including Heavier Aromatics.

I have also observed that the weight ratio of $C_8$-Aromatics/Toluene/Benzene in the co-product naphtha does not vary substantially from diverse feedstocks to the pyrolysis system. With respect to the above Table I, the weight ratio is 1.0/3.8/6.6. A similar ratio for an additional feedstock is given in Table II hereinafter presented.

Briefly, the present process involves admixing the feed to the pyrolysis furnace with a paraffinic raffinate resulting from a subsequent aromatics separation facility. Pyrolysis conditions include pressures from atmospheric to about 40.0 psig. (3.72 atm.) and temperatures in the range of about 1000° F. (537.8° C.) to about 2,000° F. (1093.3° C.), and most generally from 1,200° F. (648.9° C.) to about 1,800° F. (982.2° C.). The effluent from the pyrolysis furnace is separated into a variety of component streams.

Separation facilities are employed primarily to segregate normally vaporous material from normally liquid material. The use of these terms herein connote that a hydrocarbon which is liquid at 60° F. (15.6° C.) and atmospheric pressure, is normally liquid; if its state is that of a vapor, it is considered to be normally vaporous. Although wide latitude is available in separating the pyrolysis material, three specific individual streams are to be included. These are: (i) a hydrogen-rich vaporous phase, (ii) an ethylene product concentrate and (iii) a normally liquid stream containing the aromatic hydrocarbons. The hydrogen-rich phase will be very low in $C_2$-plus material, being about 70-80% hydrogen and 20-30% methane. In those pyrolysis operations characterized by the use of steam, the hydrogen-rich stream will contain up to about 1.0% carbon oxides. For the purposes of the present combination process, the pyrolysis system can function with or without the use of steam.

The separated normally liquid stream, which may or may not contain pentanes, is admixed with a portion of the hydrogen-rich vaporous phase and introduced into a hydrogenation, or hydrotreating facility. Since the feedstock will generally contain sulfurous compounds in addition to olefinic material, the hydrotreating system will most often consist of two stages. The first stage functions to saturate olefins without attendant saturation of aromatic nuclei. Operating conditions include temperatures from 350° F. (176.7° C.) to about 450° F. (232.2° C.), pressures from about 700 psig. (48.6 atm.) to 1000 psig. (69.1 atm.) and a liquid hourly space velocity of about two to about five. The second stage converts sulfurous compounds into hydrogen sulfide and hydrocarbons, and the operating conditions include temperatures from 650° F. (343.3° C.) to 780° F. (415.6° C.), pressures from 750 psig. (52.1 atm.) to 950 psig. (65.6 atm.) and a liquid hourly space velocity of about two to about five. Hydrogenation is effected catalytically, and any suitable catalyst described in the prior art may be employed herein. These include metals from Groups VI-B and VIII of the Periodic Table, composited with a suitable refractory carrier material such as gamma alumina.

Preferably, the hydrogenation system will be inclusive of facilities for the removal of hydrogen sulfide, normally vaporous material and a substantial portion of the hydrocarbons boiling below benzene. In one embodiment of this invention, a portion of the $C_7$-plus material is recovered and introduced into the hydrodealkylation zone.

The remainder of the hydrogenated effluent is introduced into a suitable aromatic separation system which recovers an aromatic concentrate and provides a paraffinic raffinate for recycle to the thermal cracking zone. Aromatic hydrocarbon separation may employ one or more fractionation columns, or an extractive distillation systems which utilizes an aromatic-selective solvent such as a polyethylene glycol, or a sulfolane-type organic compound. Aromatic separation systems are thoroughly documented in the prior art, and the precise method employed herein forms no essential feature of the present invention. From the standpoint of capital investment and efficiency of separation, the extractive distillation technique would be preferred. Benzene is recovered in a concentrated stream by way of a relatively simple fractionation system; higher aromatics are introduced into the dealkylation zone in admixture with a second portion of the hydrogen-rich vaporous phase.

As is well known in the art of petroleum refining, hydrodealkylation may be effected either catalytically, or thermally. With respect to the present invention, either method will be suitable although a preference exists for thermal dealkylation. Regardless, dealkylation can be operated at conditions compatible with those imposed upon the pyrolysis furnace. Thus, temperatures will range from 1000° F. (537.8° C.) to about 2,000° F. (1093.3° C.) and pressures from about atmospheric to about 1000 psig. (69.1 atm.), with 15 psig. (2.0 atm.) to about 500 psig. (35.0 atm.) being preferred. The hydrogen rate to the thermal dealkylation zone can be maintained at a very low level which is necessarily slightly in excess of that required to saturate the alkyl groups removed and to supplant the removal of the same from the aromatic nucleus. The dealkylation zone effluent can be combined with the aforementioned effluent from the hydrotreating facility and introduced into the aromatics separation system in admixture therewith, or the dealkylation zone effluent can be combined with the aforementioned aromatics concentrate and further treated in admixture therewith for the separation and recovery of benzene.

Further description of the combination process encompassed by my inventive concept will be made in conjunction with the accompanying drawing which is presented as a simplified schematic flow diagram. Miscellaneous appurtenances, not believed required by those possessing the requisite expertise in the petroleum and petrochemical areas, have been eliminated. Details such as pumps, compressors, controls and instrumentation, heat-recovery and start-up circuits, valving, coolers, condensers and other such hardware, are well within the purview of those skilled in the art.

It is not intended that the drawing as presented be construed as limiting upon the present invention, the scope and spirit of which is defined by the appended claims. As hereinbefore stated, the present process is capable of processing diverse naphthas while achieving hydrogen self-sufficiency. Table II following illustrates the results when processing a full boiling range naphtha in the pyrolysis furnace:

TABLE II

| Full Boiling Range Naphtha | |
|---|---|
| Hydrocarbon Feed Types | Wt. % |
| Paraffins | 69 |
| Naphthenes | 18 |
| Aromatics | 13 |
| Yields, Based on Feed | |
| Benzene | 9.8 |
| Toluene | 3.5 |
| $C_8$-Plus Aromatics | 1.7 |
| Total Liquid | 23.0 |
| Pyrolysis Hydrogen | 0.9 |

Hydrogenation of the total liquid pyrolysis gasoline requires about 0.25% by weight of hydrogen based upon the pyrolysis feed, while the $C_7$-plus aromatics (containing about 5.0% non-aromatics) requires about 0.18%, for a total chemical consumption of hydrogen of 0.43% by weight of pyrolysis feed. Conservative solution losses and venting are about 0.3% by weight of pyrolysis feed, for an overall hydrogen consumption of about 0.73% by weight of pyrolysis feed.

DESCRIPTION OF DRAWING

With specific reference now to the drawing, the full boiling range naphtha is introduced via line 1, admixed with a paraffinic raffinate in line 2 and passed into pyrolysis furnace 3. Thermal cracking of the feed stream is effected at a temperature of about 1,600° F. (871.1° C.) and a pressure of about 20.0 psig. (2.4 atm.). Pyrolysis effluent in line 4 is continued through line 4 into a separation facility 6.

A hydrogen-rich (about 77.0%) phase is withdrawn via conduit 7, and a portion thereof is diverted through line 13 to hydrotreating zone 14. The remainder of the hydrogen-rich phase continues through conduit 17 for introduction into thermal dealkylation furnace 23. In those rare instances in which the pyrolysis naphtha charge stock is overly rich in aromatics, make-up hydrogen may become necessary; this is introduced via line 8. In virtually all situations, however, such an external hydrogen source will be required only for start-up purposes.

For the purposes of the present illustration, a methane-rich stream is recovered from separation facility 6 by way of conduit 9, and may be burned as fuel or transported to a suitable SNG (Synthetic Natural Gas) plant for further processing. Ethylene product is shown as being recovered through conduit 10, while a $C_3/C_4$ concentrate is withdrawn via line 11. The $C_3/C_4$ concentrate can be further separated into $C_3$ and $C_4$ streams; the $C_3$ stream can be further processed to recover pure propylene, to produce cumene via alkylation with benzene or to yield LPG product; the $C_4$ stream can be further processed for recovery of purified butadiene and the olefinic residual $C_4$'s can be alkylated with isobutane for production of normally liquid motor fuel alkylate. Alternatively, the $C_3/C_4$ concentrate, after removal or saturation of diolefins, can be employed as feedstock to an acidic catalytic polymerization system for production of motor fuel polymer. Ethane and propane from the aforementioned operations can be recycled to pyrolysis. Pentanes and heavier normally liquid hydrocarbons are recovered as a bottoms stream in conduit 12, admixed with a portion of the hydrogen-rich vaporous phase from line 13 and introduced therewith into hydrotreating system 14. Herein, olefinic material is saturated and sulfurous compounds are converted to hydrogen sulfide and hydrocarbons. In the present illustration, hydrotreating system 14 includes separation facilities for recovering pentanes and lower-boiling material in line 15, and the greater proportion of $C_7$-plus material in line 16.

Benzene concentrate, containing a minor proportion of the $C_7$-plus material in addition to non-aromatics, is recovered in line 18 and introduced into an aromatic recovery zone 19. The latter utilizes a sulfolane-type organic solvent to recover substantially pure aromatics in line 20 and to reject non-aromatic raffinate in line 2. The latter is recycled via lines 2 and 1 into the pyrolysis furnace 3. The former passes through line 20 into fractionation zone 21, with the benzene product being recovered via conduit 22. Heavier aromatic hydrocarbons are withdrawn as a bottoms stream in line 17, admixed with the $C_7$-plus stream in line 16 and recycled to thermal dealkylation furnace 23. The latter functions at a temperature of about 1550° F. (843.3° C.) and a pressure of about 25 psig (2.7 atm.), which conditions are compatible with those imposed upon pyrolysis furnace 3. The total product effluent from the hydrodealkylation reaction zone is passed by way of line 5 to a gas-liquid separation zone 24 wherein the normally gaseous hydrocarbon phase is separated overhead through line 25. A normally liquid hydrocarbon phase is recovered through line 26 and combined with the aforementioned benzene concentrate in line 18 to be introduced into the above-described aromatic recovery zone 19. Alternatively, although not shown, the normally liquid hydrocarbon phase recovered through line 26 can be routed to bypass the aromatics recovery zone 19 and combine with the aromatic stream in line 20 and further treated in the fractionation zone 21.

The foregoing specification, particularly when viewed in conjunction with the accompanying drawing, clearly illustrates the method of effecting the process encompassed by the present invention and the benefits afforded through the utilization thereof.

I claim as my invention:

1. A process for the co-production of ethylene and benzene from a hydrocarbonaceous feedstock which comprises:
    (a) charging said feedstock to a thermal cracking zone at conditions selected to convert paraffinic hydrocarbons into lower boiling, normally vaporous, hydrocarbons;
    (b) introducing the thermal cracking zone effluent into a first separation zone and separating a hydrogen-rich vaporous phase, ethylene, and a normally liquid phase containing aromatic hydrocarbons;
    (c) recovering the separated ethylene;
    (d) introducing said normally liquid phase into a second separation zone, concentrating the aromatic hydrocarbons therein, and separating unconverted non-aromatic hydrocarbons;
    (e) introducing said aromatic hydrocarbons into a third separation zone and separating benzene and alkylaromatic hydrocarbons therein;
    (f) recovering the separated benzene;
    (g) reacting said alkylaromatic hydrocarbons in admixture with at least a portion of said hydrogen-rich vaporous phase in a dealkylation reaction zone at conditions selected to convert said alkylaromatic hydrocarbons into benzene; and,
    (h) introducing the dealkylation zone effluent into said second separation zone in combination with the aforesaid normally liquid phase introduced thereto.

2. The process of claim 1 further characterized in that said hydrocarbonaceous feedstock is a normally liquid feedstock containing hydrocarbons boiling up to about 525° F.

3. The process of claim 1 further characterized in that said hydrocarbonaceous feedstock is a light naphtha fraction having an end boiling point in the range of from about 200° to about 300° F.

4. The process of claim 1 further characterized in that said hydrocarbonaceous feedstock is a heavy naphtha fraction having an initial boiling point in excess of about 200° F. and an end boiling point in excess of about 300° F.

5. The process of claim 1 further characterized in that said unconverted non-aromatic hydrocarbons are admixed with said feedstock and subjected therewith to thermal cracking.

6. The process of claim 1 further characterized in that said thermal cracking is effected at a temperature of from about 1000° to about 2000° F. and at a pressure of from about atmospheric to about 40 psig.

7. The process of claim 1 further characterized in that said dealkylation conditions include a temperature of from about 1000° to about 1500° F. and a pressure of from about 15 to about 500 psig.

8. The process of claim 1 further characterized in that said dealkylation of said alkylaromatic hydrocarbons is non-catalytic.

9. The process of claim 1 further characterized in that said dealkylation of said alkylaromatic hydrocarbons is catalytic.

10. The process of claim 1 further characterized with respect to step (h) in that said dealkylation zone effluent is introduced into a gas-liquid separation zone wherein a vapor phase comprising normally gaseous hydrocarbons is separated, and a normally liquid hydrocarbon phase is recovered and introduced into said second separation zone in combination with the aforesaid normally liquid phase introduced thereto.

11. The process of claim 1 further characterized with respect to step (h) in that said dealkylation zone effluent is introduced into a gas-liquid separation zone wherein a vapor phase comprising normally gaseous hydrocarbons is separated, and a normally liquid hydrocarbon phase is recovered and introduced into said third separation zone in combination with the aforesaid aromatic hydrocarbons introduced thereto.

12. A process for the co-production of ethylene and benzene from a hydrocarbonaceous feedstock which comprises:
 (a) charging said feedstock to a thermal cracking zone at conditions selected to convert paraffinic hydrocarbons into lower boiling, normally vaporous hydrocarbons;
 (b) introducing the thermal cracking zone effluent into a first separation zone and separating a hydrogen-rich vaporous phase, ethylene, and a normally liquid phase containing aromatic hydrocarbons;
 (c) recovering the separated ethylene;
 (d) treating said normally liquid phase in admixture with a portion of said hydrogen-rich vaporous phase in a hydrotreating zone at hydrotreating conditions selected to saturate olefins and convert sulfurous compounds to hydrogen sulfide and hydrocarbons, separating hydrogen sulfide and recovering the hydrotreated normally liquid phase;
 (e) introducing said hydrotreated normally liquid phase into a second separation zone, concentrating the aromatic hydrocarbons therein, and separating unconverted non-aromatic hydrocarbons;
 (f) introducing said aromatic hydrocarbons into a third separation zone and separating benzene and alkylaromatic hydrocarbons therein;
 (g) recovering the separated benzene;
 (h) reacting with alkylaromatic hydrocarbons in admixture with at least a portion of said hydrogen-rich vaporous phase in a dealkylation reaction zone at conditions selected to convert said alkylaromatic hydrocarbons into benzene; and,
 (i) introducing the dealkylation zone effluent into said second separation zone in combination with the aforesaid hydrotreated normally liquid phase introduced thereto.

13. The process of claim 12 further characterized with respect to step (i) in that said dealkylation zone effluent is introduced into a gas-liquid separation zone wherein a vapor phase comprising normally gaseous hydrocarbons is separated, and a normally liquid hydrocarbon phase is recovered and introduced into said second separation zone in combination with the aforesaid hydrotreated normally liquid phase introduced thereto.

14. The process of claim 12 further characterized with respect to step (i) in that said dealkylation zone effluent is introduced into a gas-liquid separation zone wherein a vapor phase comprising normally gaseous hydrocarbons is separated, and a normally liquid hydrocarbon phase is recovered and introduced into said third separation zone in combination with the aforesaid aromatic hydrocarbons introduced thereto.

* * * * *